United States Patent
Orhan et al.

(10) Patent No.: US 10,537,737 B2
(45) Date of Patent: Jan. 21, 2020

(54) ADAPTIVE NON-INVASIVE ALTERNATING CURRENT BRAIN STIMULATION SYSTEM AND METHOD

(71) Applicant: HONEYWELL INTERNATIONAL INC., Morris Plains, NJ (US)

(72) Inventors: Umut Orhan, Kirkland, WA (US);
Santosh Mathan, Seattle, WA (US);
Michael Pavel, Boston, MA (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 134 days.

(21) Appl. No.: 15/919,439

(22) Filed: Mar. 13, 2018

(65) Prior Publication Data

US 2019/0282811 A1     Sep. 19, 2019

(51) Int. Cl.
*A61N 1/36* (2006.01)
*A61B 5/00* (2006.01)
(Continued)

(52) U.S. Cl.
CPC ...... *A61N 1/36031* (2017.08); *A61B 5/04017* (2013.01); *A61B 5/0476* (2013.01); *A61B 5/4836* (2013.01); *A61N 1/0529* (2013.01); *A61N 1/36025* (2013.01); *A61N 1/37514* (2017.08)

(58) Field of Classification Search
CPC ............ A61N 1/36025; A61N 1/36031; A61N 1/0529; A61N 1/37514; A61B 5/0476; A61B 5/4836
See application file for complete search history.

(56) References Cited

U.S. PATENT DOCUMENTS

| | | | |
|---|---|---|---|
| 6,480,743 B1 | 11/2002 | Kirkpatrick et al. | |
| 2008/0319505 A1 | 12/2008 | Boyden et al. | |
| 2016/0256105 A1* | 9/2016 | Boyle | A61M 21/00 |

FOREIGN PATENT DOCUMENTS

| | | |
|---|---|---|
| WO | 2016179240 A1 | 11/2016 |
| WO | 2016179407 A1 | 11/2016 |
| WO | 2017115368 A1 | 7/2017 |

OTHER PUBLICATIONS

Boyle, M.R. et al.; EEG Feedback-Controlled Transcranial Alternating Current Stimulation; 6th Annual International IEEE EMBS Conference on Neural Engineering, San Diego, CA Nov. 6-8, 2013.

* cited by examiner

*Primary Examiner* — Tammie K Marlen
(74) *Attorney, Agent, or Firm* — Lorenz & Kopf, LLP (57) ABSTRACT

An adaptive non-invasive alternating current brain stimulation system and method includes supplying transcranial alternating current stimulation (tACS) from a tACS source to a person, and receiving electroencephalogram (EEG) signals from EEG sensors disposed on the person, where the EEG signals including stimulation interference. The received EEG signals are processed using an adaptive model to estimate the stimulation interference in the EEG signals. The estimated stimulation interference is subtracted from the EEG signals to estimate neural oscillations of the person. The estimated neural oscillations are processed through an autoregressive model to generate predictions of future neural activity of the person and, based on the generated predictions, one or more electrical characteristics of the tACS being supplied to the person are varied to thereby modulate the neural oscillations of the person.

20 Claims, 3 Drawing Sheets

(51) Int. Cl.
*A61B 5/04* (2006.01)
*A61B 5/0476* (2006.01)
*A61N 1/375* (2006.01)
*A61N 1/05* (2006.01)

ADAPTIVE NON-INVASIVE ALTERNATING CURRENT BRAIN STIMULATION SYSTEM AND METHOD

STATEMENT REGARDING FEDERALLY SPONSORED RESEARCH OR DEVELOPMENT

This invention was made with Government support under Contract No. 2014-13121700007 awarded by the Intelligence Advanced Research Project Agency ("IARPA"). The Government has certain rights in the invention.

TECHNICAL FIELD

The present invention generally relates to brain stimulation systems and methods, and more particularly relates to an adaptive non-invasive alternating current brain stimulation system and method.

BACKGROUND

Non-invasive brain stimulation (NIBS) has been used extensively to modulate brain activity, often with the goal of enhancing learning or performance. Depending on the characteristics of the current used, electrical stimulation can either enhance, or inhibit cortical excitability.

Cognitive enhancement, most notably using non-invasive brains stimulation (NIBS), is a rapidly increasing market. While there are different ways to modulate brain activity using NIBS, direct manipulation of ongoing brain oscillations remains an important objective for many researchers. This has typically been done by means of a strong exogenously imposed signal to which internal oscillations couple in phase. An alternative approach is to attenuate or amplify endogenous oscillations using external stimulation that is either tailored to be in phase (to amplify endogenous oscillations) or out of phase with endogenous EEG signals (to attenuate endogenous oscillations). However, tailoring of stimulation to endogenous signals is challenging because the stimulation noise overwhelms these weak signals.

Hence, there is a need for a system and method of cognitive training that can tailor the stimulation to endogenous signals despite the stimulation noise in the signals. The present invention addresses at least this need.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

In one embodiment, an adaptive non-invasive alternating current brain stimulation method includes supplying transcranial alternating current stimulation (tACS) from a tACS source to a person, and receiving electroencephalogram (EEG) signals from EEG sensors disposed on the person, where the EEG signals including stimulation interference. The received EEG signals are processed using an adaptive model to estimate the stimulation interference in the EEG signals. The estimated stimulation interference is subtracted from the EEG signals to estimate neural oscillations of the person. The estimated neural oscillations are processed through an autoregressive model to generate predictions of future neural activity of the person and, based on the generated predictions, one or more electrical characteristics of the tACS being supplied to the person are varied to thereby modulate the neural oscillations of the person.

In another embodiment, an adaptive non-invasive alternating current brain stimulation system includes a transcranial alternating current stimulation (tACS) source, a plurality of electroencephalogram (EEG) sensors, and a processing system. The tACS source is configured to supply tACS to a person. The EEG sensors are each configured to be disposed on the person and, in response to neural oscillations of the person, to supply EEG signals representative thereof, where the EEG signals including stimulation interference. The processing system is coupled to the tACS source and is further coupled to receive the EEG signals from the EEG sensors. The processing system is configured, upon receipt of the EEG signals, to: implement an adaptive model to estimate the stimulation interference in the EEG signals; subtract the estimated stimulation interference from the EEG signals to estimate the neural oscillations of the person; process the neural oscillations of the person through an autoregressive model to generate predictions of future neural activity of the person; and based on the generated predictions, command the tACS source to vary one or more electrical characteristics of the tACS being supplied to the person, to thereby modulate the neural oscillations of the person.

In yet another embodiment, an adaptive non-invasive alternating current brain stimulation system includes a transcranial alternating current stimulation (tACS) source, a plurality of electroencephalogram (EEG) sensors, and a processing system. The tACS sours is configured to supply tACS to a person. Each EEG sensor is configured to be disposed on the person and, in response to neural oscillations of the person, to supply EEG signals representative thereof, the EEG signals including stimulation interference. The processing system is coupled to the tACS source and further is coupled to receive the EEG signals from the EEG sensors. The processing system is configured, upon receipt of the EEG signals, to: amplify, digitize, and filter the received EEG signals; implement an adaptive model to estimate the stimulation interference in the amplified, digitized, and filtered EEG signals; subtract the estimated stimulation interference from the amplified, digitized, and filtered EEG signals to estimate the neural oscillations of the person; process the neural oscillations of the person through an autoregressive model to generate predictions of future neural activity of the person; and based on the generated predictions, command the tACS source to vary one or more of phase, frequency, and amplitude of the tACS being supplied to the person, to thereby modulate the neural oscillations of the person.

Furthermore, other desirable features and characteristics of the adaptive non-invasive alternating current brain stimulation system and method will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
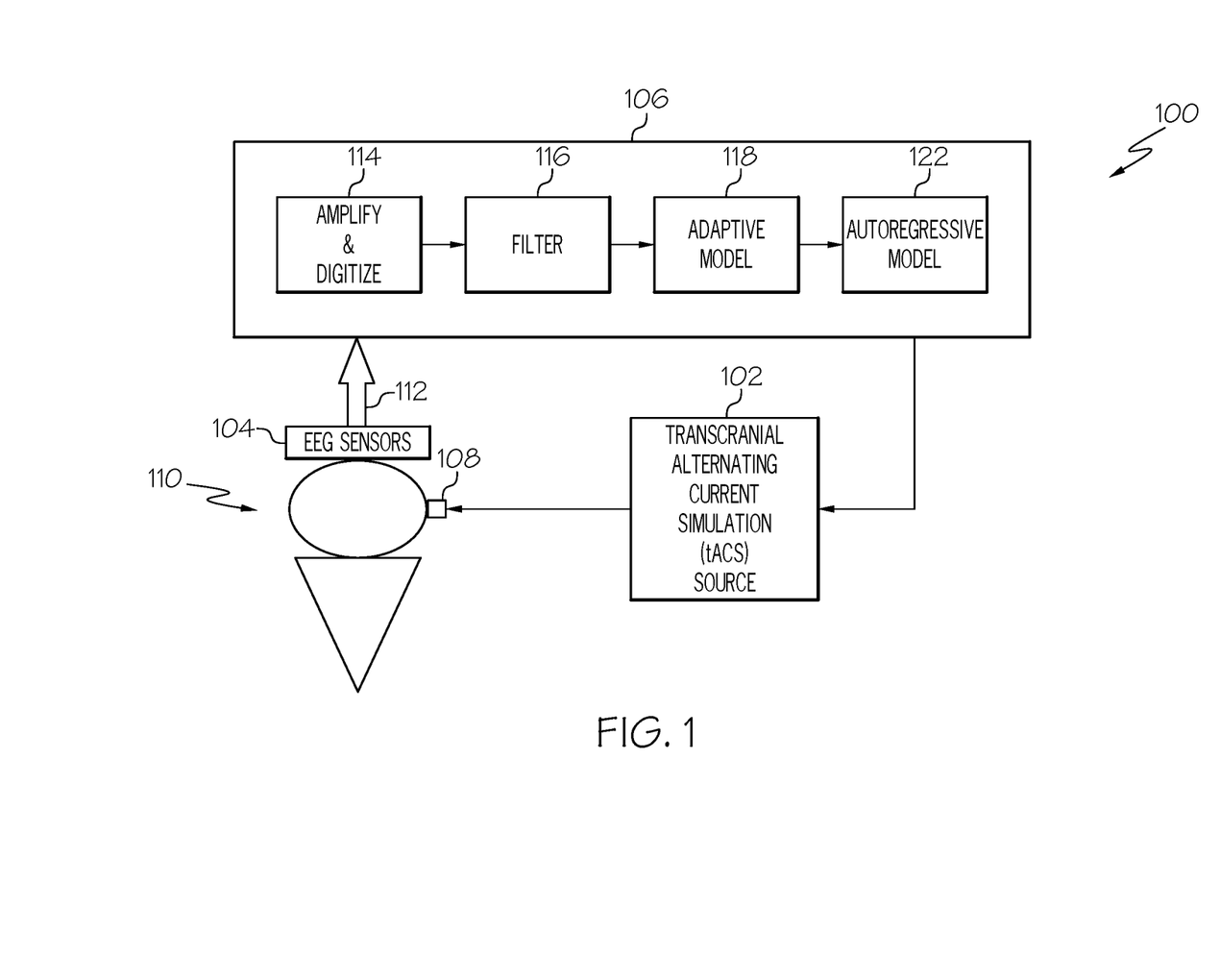
FIG. 1 depicts a functional block diagram of one embodiment of an adaptive non-invasive alternating current brain stimulation system.

Referring first to FIG. 1, a functional block diagram of one embodiment of an adaptive non-invasive alternating current brain stimulation system 100 is depicted. The depicted system 100 includes a transcranial alternating current stimulation (tACS) source 102, a plurality of electroencephalogram (EEG) sensors 104, and a processing system 106. The tACS source 102 is configured to supply a relatively low-intensity sinusoid current (i.e., tACS signal), via one or more electrodes 108, to a person 110. As is generally known, the resulting electric field modulates neuronal network activity in the brain of the user 110, resulting in what are referred to as neural oscillations.

The EEG sensors 104 are each configured to be disposed on the person 110. Indeed, in FIG. 1, the EEG sensors 104 are depicted as being disposed on the person's head. Each EEG sensor 104 is configured, in response to neural oscillations of the person 110, to supply EEG signals 112 representative of the person's neural oscillations to the processing system 106. As may be readily appreciated by persons of skill in the art, the EEG signals 112 supplied from the EEG sensors 104 include stimulation interference.

The processing system 106 is coupled to the tACS source 102 and to the EEG sensors 104. The processing system 106 is coupled to receive the EEG signals 112 from the EEG sensors 104 and is configured, in response to the received EEG signals 112, to implement various processing functions and to command to the tACS source 102, based on the various processing functions, to vary one or more electrical characteristics of the tACS being supplied to the person 110, and thereby modulate the neural oscillations of the person 110.

Before proceeding further, it is noted that the processing system 106, as used herein, generally represents the hardware, software, and/or firmware components configured to facilitate communications and/or interaction between the elements of the system 100 and perform additional tasks and/or functions to support operation of the system 100, as described in greater detail below. Depending on the embodiment, the processing system 106 may be implemented or realized with a general-purpose processing system, a content addressable memory, a digital signal processing system, an application specific integrated circuit, a field programmable gate array, any suitable programmable logic device, discrete gate or transistor logic, processing core, discrete hardware components, or any combination thereof, designed to perform the functions described herein. The processing system 106 may also be implemented as a combination of computing devices, e.g., a plurality of processing cores, a combination of a digital signal processing system and a microprocessing system, a plurality of microprocessing systems, one or more microprocessing systems in conjunction with a digital signal processing system core, or any other such configuration. In practice, the processing system 106 includes processing logic and signal conditioning functions that may be needed to carry out the functions, techniques, and processing tasks associated with the operation of the system 100, as described in greater detail below. Furthermore, the steps of a method or algorithm described in connection with the embodiments disclosed herein may be embodied directly in hardware, in firmware, in a software module executed by the processing system 106, or in any practical combination thereof. For example, in one or more embodiments, the processing system 106 may include or otherwise access a data storage element (or memory), which may be realized as any sort of non-transitory short or long term storage media capable of storing programming instructions for execution by the processing system 106. The code or other computer-executable programming instructions, when read and executed by the processing system 106, cause the processing system 106 to support or otherwise perform certain tasks, operations, functions, and/or processes described herein.

Returning now to the description, the various processing functions that the processing system 106 implements may vary. The processing functions include at least estimating the underlying neural oscillations of the person 110 from the EEG signals 112, and generating predictions of future neural activity of the person 110. As FIG. 1 depicts, the processing functions, at least in the depicted embodiment, may also include amplification and digitization 114, and filtering 116 of the received EEG signals 112.

The amplification and digitization function 114 and the filtering function 116 may be implemented using any one of numerous known amplification, analog-to-digital conversion (A/D) techniques, and any one of numerous known filtering approaches and\ configurations. Preferably, however, the filter function 116 is implemented as a bandpass filter that will pass the frequency band of interest in the received EEG signals (e.g., φ waves—4-8 Hz; α waves—8-12 Hz; (β waves-×12 Hz). As may be appreciated the passband of the filter may be adjustable to vary the frequency band of interest.

The EEG signals 112, even after amplification, digitization, and filtering, include not only the underlying signal of interest—the EEG activity that represents the neural oscillations of the person—but also components corresponding to stimulation interference. The primary challenge in estimating the underlying signal of interest is that the stimulation interference may be 10,000 times larger (80 dB) in amplitude than the signal of interest. Thus, to estimate the underlying neural oscillations of the person 110 in the EEG signals 112, the processing system 106 is configured to implement an adaptive model 118. The adaptive model 118 estimates the stimulation interference in the EEG signals 112, and then subtracts the estimated stimulation interference from the EEG signals 112. The result, as may be appreciated, is in an estimate of the neural oscillations of the person 110.

To implement the above-described function, the adaptive model 118 assumes (correctly) that the tACS signal ($S_t$) supplied to the person 110 has the following sinusoid form:

$S_t = A \cos(\omega t + \varnothing)$ where: A is the stimulation intensity/amplitude,
ω is the stimulation frequency, and
φ is the stimulation phase.

As already noted, the EEG signals 112 supplied from the EEG sensors 102 ($EEG_{measurement}(t)$) include the underlying EEG of interest ($EEG_{interest}(t)$) and stimulation interference (I(t)). Thus, the model 118 additionally assumes the received EEG signals to be in the following form:

$EEG_{measurement}(t) = EEG_{interest}(t) + I(t)$.

The model 118 further assumes that the stimulation interference (I(t)) is in the following form:

$I_t = ARt_1 \cos(\omega t + \varnothing + \theta t_1) + ARt_2 \cos(2\omega t + \varnothing + \theta t_2) + ARt_3 \cos(3\omega t + \varnothing + \theta t_3) + \ldots$ where: the first term represents the fundamental component of the stimulation interference, and the remaining terms represent the harmonics,
$Rt_n$ represent scaling coefficients analogous to impedance, and
$\theta t_n$ represent phase shifts relative to the signal source.

It is noted that the scaling coefficients ($Rt_n$) depend on the connectivity of the EEG sensors 104, gel pathways on the scalp of the person 110, and the current pathways through the brain. As conductivity changes via, for example, the sweating of the person 110, electrode connection changes, or drying of the gel, the scaling coefficients ($Rt_n$) are expected to change slowly over time. The phase shifts ($\theta t_n$) are also expected to change slowly over time, and may occur due to group delays in the filter, clock drifts, nonlinearities in the skull/brain and current pathways.

The adaptive model 118 adaptively estimates the scaling coefficients ($Rt_n$) and phase shifts ($\theta t_n$), via a recursive least squares error technique that employs exponential forgetting, to estimate the stimulation interference (I(t)). The processing system 106 then subtracts the estimated stimulation interference from the from the measured EEG signals 112 ($EEG_{measurement}(t)$) to estimate the underlying EEG of interest ($EEG_{interest}(t)$). That is, the neural oscillations of the person 110.

The processing system 106 may additionally be configured, at least in some embodiments, to command (and thereby control) the tACS source 102 to modulate the intensity/amplitude of the tACS signal being supplied to the person 110. This modulation, when implemented, resolves any ambiguity between the estimated stimulation interference I(t) and the measured EEG signals 112 ($EEG_{measurement}(t)$ at the stimulation frequency (ω) and the harmonic frequencies (2ω, 3ω, 4ω, ... ). The modulation may be random or non-random, and may be implemented using any one of numerous functional waveform types. In one embodiment, however, the processing system 106 is configured to command the tACS source 102 to modulate the intensity of the tACS signals via a randomly varying staircase function. For example, the tACS signals may randomly between 400 and 500 uA with a 15 s period. If the stimulation intensity is not modulated (randomly or non-randomly), this can, in some embodiments, cause the components of the EEG signals 112 at the stimulation and harmonic frequencies to be eliminated completely, causing a significant loss of information in the underlying EEG of interest ($EEG_{interest}(t)$).

The processing system 106 is further configured to process the neural oscillation estimates of the person 110 to generate predictions of the future neural activity of the person 110. One of the main reasons for this is that the characteristics of the underlying EEG of interest ($EEG_{interest}$(t)) change over time. When the stimulation frequency and phase are modulated, it is desirable to attenuate or amplify the EEG activity during the corresponding stimulation section. Hence, it is important for the stimulation parameters to reflect the present, not the past, EEG activity.

To implement this function, the processing system 106 is configured to process the neural oscillations of the person 110 through any one of numerous linear or non-linear prediction algorithms, such as an autoregressive model 122. In particular, an autoregressive model 122 is fit to the most recent window of EEG samples to generate predictions of the future neural activity of the person 110. Future EEG samples are predicted by applying the corresponding autoregressive filter 122. The predictions are possible because of the narrow-band nature of the EEG signals used to control the stimulator Thereafter, and as FIG. 1 further depicts, the processing system 106 is further configured, based on the generated predictions of the future neural activity, to command the tACS source 102 to vary one or more electrical characteristics of the tACS being supplied to the person 110. The one or more electrical characteristics may vary, and may include one or more of phase, frequency, and amplitude. Regardless of the specific electrical characteristics that are varied, the electrical characteristics are varied to amplify and/or attenuate the neural oscillations of the person 110. In other words, the electrical characteristics are varied to modulate the neural oscillations of the person 110. Thus, as may be appreciated, the processing system 106 is further configured to apply a sinusoid to the future neural activity predictions, and the corresponding frequency, phase, and/or amplitude parameters are updated.

Figure 2:
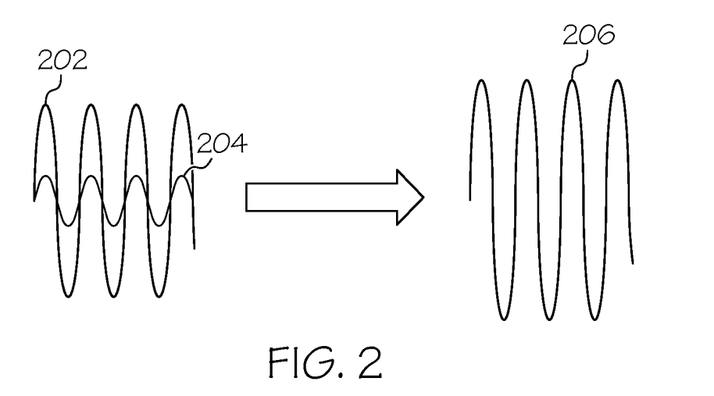
FIGS. 2 and 3 depict simplified versions of example waveforms to illustrate how the system of FIG. 1 may modulate the neural oscillations of a person to amplify and attenuate, respectively, neural activity.
Figure 3:
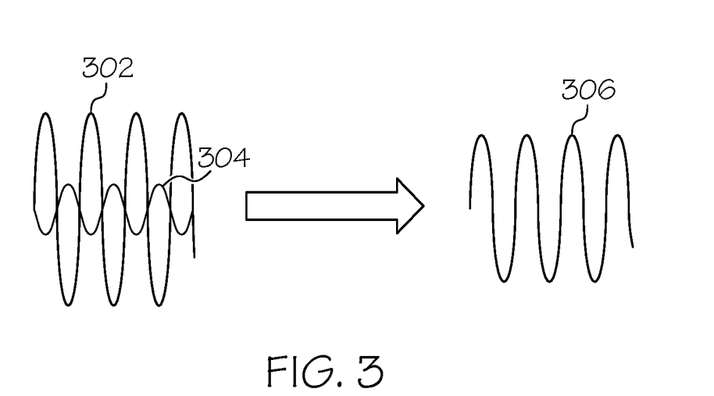

To illustrate, in a simplified manner, how the varying the electrical characteristics of the tACS may modulate the neural oscillations, reference should be made to FIGS. 2 and 3. As FIG. 2 depicts, to amplify the neural oscillations in a desired frequency band, the frequency and phase of the tACS 202 are matched to the predictions of the future neural activity 204 to achieve a stimulation 206 that amplifies the imminent oscillatory activity of interest. As FIG. 3 depicts, to attenuate the neural oscillations in a desired frequency band, the frequency of the stimulation 302 is modulated to match to the predictions of the future neural activity, but the phase is modulated to correspond to a 180-degree shift with the imminent oscillatory activity of interest 304 to achieve a stimulation 306 that attenuates the imminent oscillatory activity of interest.

Figure 4:
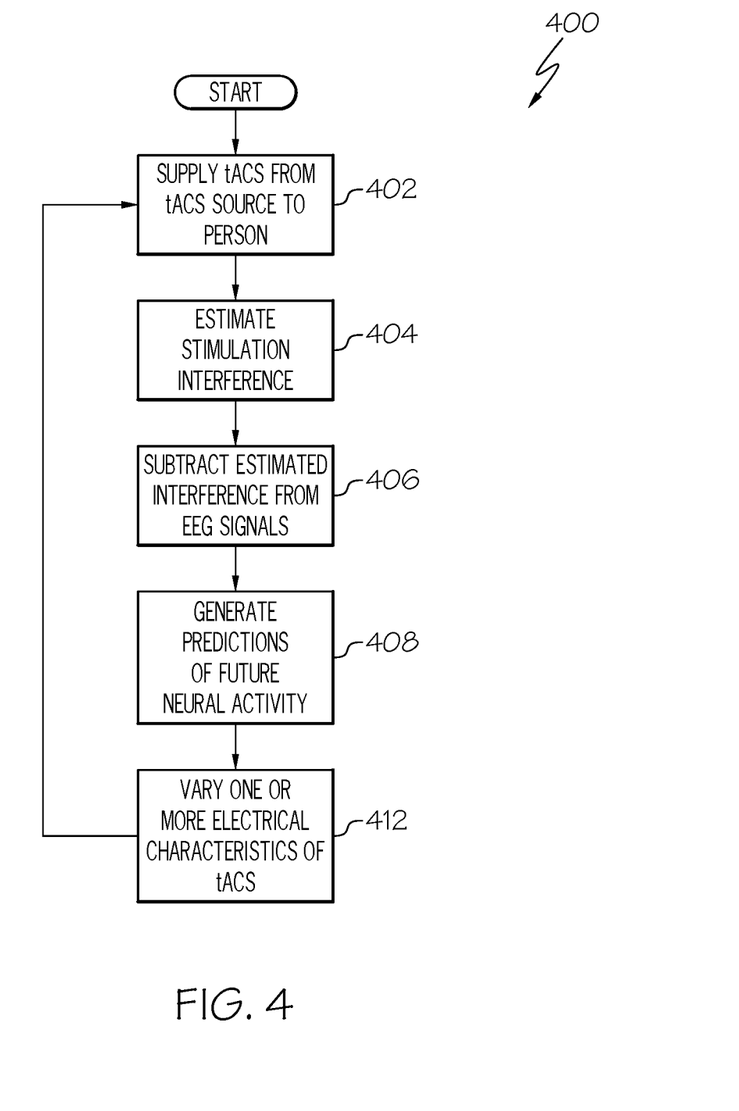
FIG. 4 depicts a process, in flowchart form, that may be implemented in the system of FIG. 1 to modulate the neural oscillations of a person.

The adaptive non-invasive alternating current brain stimulation process that is implemented in the system 100 and is described above is depicted in flowchart form in FIG. 4, and for completeness will now be described. The process 400 begins by supplying tACS from the tACS source 102 to the person 110 (402). The processing system 106 receives the EEG signals 112 from the EEG sensors 1104 disposed on the person 110, and processes the received EEG signals 112 using an adaptive model 118 to estimate the stimulation interference in the EEG signals 112 (404). The estimated stimulation interference is subtracted from the EEG signals 112 to estimate the neural oscillations of the person 110 (408). The estimated neural oscillations are processed through the autoregressive model 122 to generate predictions of future neural activity of the person (408). Then, based on the generated predictions, one or more electrical characteristics of the tACS being supplied to the person 110 are varied, to thereby modulate the neural oscillations of the person (412).

The system and method described herein provides a safe, practical, and broadly applicable technique for enhancing human performance. The system and method have been demonstrated to enhance fluid intelligence (measured using IQ tests) in randomized, placebo-controlled, multi-site studies.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessing systems or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processing system, a digital signal processing system (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processing system may be a microprocessing system, but in the alternative, the processing system may be any conventional processing system, controller, microcontroller, or state machine. A processing system may also be implemented as a combination of computing devices, e.g., a combination of a DSP and a microprocessing system, a plurality of microprocessing systems, one or more microprocessing systems in conjunction with a DSP core, or any other such configuration.

The steps of a method or algorithm described in connection with the embodiments disclosed herein may be embodied directly in hardware, in a software module executed by a processing system, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processing system such that the processing system can read information from, and write information to, the storage medium. In the alternative, the storage medium may be integral to the processing system. The processing system and the storage medium may reside in an ASIC.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processing system devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessing systems or other control devices.

When implemented in software or firmware, various elements of the systems described herein are essentially the code segments or instructions that perform the various tasks. The program or code segments can be stored in a processing system-readable medium or transmitted by a computer data signal embodied in a carrier wave over a transmission medium or communication path. The "computer-readable medium", "processing system-readable medium", or "machine-readable medium" may include any medium that can store or transfer information. Examples of the processing system-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

Some of the functional units described in this specification have been referred to as "modules" in order to more particularly emphasize their implementation independence. For example, functionality referred to herein as a module may be implemented wholly, or partially, as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like. Modules may also be implemented in software for execution by various types of processing systems. An identified module of executable code may, for instance, comprise one or more physical or logical modules of computer instructions that may, for instance, be organized as an object, procedure, or function. Nevertheless, the executables of an identified module need not be physically located together, but may comprise disparate instructions stored in different locations that, when joined logically together, comprise the module and achieve the stated purpose for the module. Indeed, a module of executable code may be a single instruction, or many instructions, and may even be distributed over several different code segments, among different programs, and across several memory devices. Similarly, operational data may be embodied in any suitable form and organized within any suitable type of data structure. The operational data may be collected as a single data set, or may be distributed over different locations including over different storage devices, and may exist, at least partially, merely as electronic signals on a system or network.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. An adaptive non-invasive alternating current brain stimulation method, comprising the steps of:
    supplying transcranial alternating current stimulation (tACS) from a tACS source to a person;
    receiving electroencephalogram (EEG) signals from EEG sensors disposed on the person, the EEG signals including stimulation interference;
    processing the received EEG signals using an adaptive model to estimate the stimulation interference in the EEG signals;
    subtracting the estimated stimulation interference from the EEG signals to estimate neural oscillations of the person;
    processing the estimated neural oscillations through an autoregressive model to generate predictions of future neural activity of the person; and
    based on the generated predictions, varying one or more electrical characteristics of the tACS being supplied to the person to thereby modulate the neural oscillations of the person.

2. The method of claim 1, further comprising:
    amplifying and digitizing the received EEG signals before processing the received EEG signals using the adaptive model.

3. The method of claim 2, further comprising:
    filtering the received EEG signals after amplifying and digitizing the received EEG signals.

4. The method of claim 1, wherein the adaptive model implements a recursive least squares estimation algorithm with exponential forgetting to adaptively estimate scaling factors and phase shifts in the stimulation interference.

5. The method of claim 1, further comprising:
    modulating an intensity of the tACS being supplied to the person to resolve ambiguity between the estimated stimulation interference and the EEG signals.

6. The method of claim 5, wherein the step of modulating comprises modulating the intensity of the tACS via a randomly varying staircase function.

7. The method of claim 1, further comprising:
    applying a sinusoidal fit to the predictions of future neural activity of the person.

8. The method of claim 1, wherein one or more electrical characteristics of the tACS include one or more of phase, frequency, and amplitude.

9. An adaptive non-invasive alternating current brain stimulation system, comprising:
    a transcranial alternating current stimulation (tACS) source configured to supply tACS to a person;
    a plurality of electroencephalogram (EEG) sensors, each EEG sensor configured to be disposed on the person and, in response to neural oscillations of the person, to supply EEG signals representative thereof, the EEG signals including stimulation interference; and
    a processing system coupled to the tACS source and further coupled to receive the EEG signals from the EEG sensors, the processing system configured, upon receipt of the EEG signals, to:
        implement an adaptive model to estimate the stimulation interference in the EEG signals;
        subtract the estimated stimulation interference from the EEG signals to estimate the neural oscillations of the person;
        process the neural oscillations of the person through an autoregressive model to generate predictions of future neural activity of the person; and
        based on the generated predictions, command the tACS source to vary one or more electrical characteristics of the tACS being supplied to the person, to thereby modulate the neural oscillations of the person.

10. The system of claim 9, wherein the processing system is further configured to:
    amplify and digitize the received EEG signals before processing the received EEG signals using the adaptive model.

11. The system of claim 10, wherein the processing system is further configured to:
    filter the received EEG signals after amplifying and digitizing the received EEG signals.

12. The system of claim 9, wherein the adaptive model implements a recursive least squares estimation algorithm with exponential forgetting to adaptively estimate scaling factors and phase shifts in the stimulation interference.

13. The system of claim 9, wherein the processing system is further configured to command the tACS source to modulate an intensity of the tACS being supplied to the person to thereby resolve ambiguity between the estimated stimulation interference and the EEG signals.

14. The system of claim 13, wherein the processing system is configured to command the tACS source to modulate the intensity of the tACS via a randomly varying staircase function.

15. The system of claim 9, wherein the processing system is further configured to apply a sinusoidal fit to the predictions of future neural activity of the person.

16. The system of claim 9, wherein the one or more electrical characteristics of the tACS include one or more of phase, frequency, and amplitude.

17. An adaptive non-invasive alternating current brain stimulation system, comprising:
  a transcranial alternating current stimulation (tACS) source configured to supply tACS to a person;
  a plurality of electroencephalogram (EEG) sensors, each EEG sensor configured to be disposed on the person and, in response to neural oscillations of the person, to supply EEG signals representative thereof, the EEG signals including stimulation interference; and
  a processing system coupled to the tACS source and further coupled to receive the EEG signals from the EEG sensors, the processing system configured, upon receipt of the EEG signals, to:
    amplify, digitize, and filter the received EEG signals;
    implement an adaptive model to estimate the stimulation interference in the amplified, digitized, and filtered EEG signals;
    subtract the estimated stimulation interference from the amplified, digitized, and filtered EEG signals to estimate the neural oscillations of the person;
    process the neural oscillations of the person through an autoregressive model to generate predictions of future neural activity of the person; and
    based on the generated predictions, command the tACS source to vary one or more of phase, frequency, and amplitude of the tACS being supplied to the person, to thereby modulate the neural oscillations of the person.

18. The system of claim 17, wherein the adaptive model implements a recursive least squares estimation algorithm with exponential forgetting to adaptively estimate scaling factors and phase shifts in the stimulation interference.

19. The system of claim 17, wherein the processing system is further configured to command the tACS source to randomly modulate an intensity of the tACS being supplied to the person, via a randomly varying staircase function, to resolve ambiguity between the estimated stimulation interference and the EEG signals.

20. The system of claim 17, wherein the processing system is further configured to apply a sinusoidal fit to the predictions of future neural activity of the person.

* * * * *